United States Patent [19]

Bonnet

[11] 4,430,996
[45] Feb. 14, 1984

[54] RESECTOSCOPES

[75] Inventor: Ludwig Bonnet, Knittlingen, Fed. Rep. of Germany

[73] Assignee: Richard Wolf GmbH, Knittlingen, Fed. Rep. of Germany

[21] Appl. No.: 180,367

[22] Filed: Aug. 22, 1980

[30] Foreign Application Priority Data

Aug. 28, 1979 [DE] Fed. Rep. of Germany ... 7924359[U]

[51] Int. Cl.$^3$ .............................................. A61B 17/36
[52] U.S. Cl. ..................................... 128/303.15; 128/4
[58] Field of Search .................. 128/4, 6, 3, 7, 303.15, 128/303.14, 303.17, 8

[56] References Cited

U.S. PATENT DOCUMENTS

| | | | |
|---|---|---|---|
| 2,448,741 | 9/1948 | Scott et al. | 128/303.15 |
| 3,315,207 | 4/1967 | Speelman | 128/4 X |
| 4,061,135 | 12/1977 | Widran et al. | 128/6 |
| 4,137,920 | 2/1979 | Bonnet | 128/7 X |

FOREIGN PATENT DOCUMENTS 2044108 10/1980 United Kingdom ................ 128/326

*Primary Examiner*—Gene Mancene
*Assistant Examiner*—Mickey Yu
*Attorney, Agent, or Firm*—Kinzer, Plyer, Dorn & McEachran

[57] ABSTRACT

This invention relates to resectoscopes of the kind comprising an optical system extending through a shaft and an HF cutting electrode which is axially displaceable by means of a guided bearer on a guide traversing the optical system and is rotatable together with the shaft around the axis of the optical system.

According to the invention, the optical system is a stereo system that provides a viewing angle of 180°, and a cylinder is provided with a fastening device to secure the proximal end of the cutting electrode. The cylinder is rotatably and axially displaceably installed within the guided bearer in the guide traversing the optical system. This guide is of polygonal cross-section and is rotatable conjointly with the cutting electrode and the shaft around the axis of the optical system. The guided bearer is complementarily guided on a parallel guide provided with a handle at the distal extremity and connected rigidly at the proximal end via a web to a coupling for connection of the stereo optical system.

3 Claims, 4 Drawing Figures

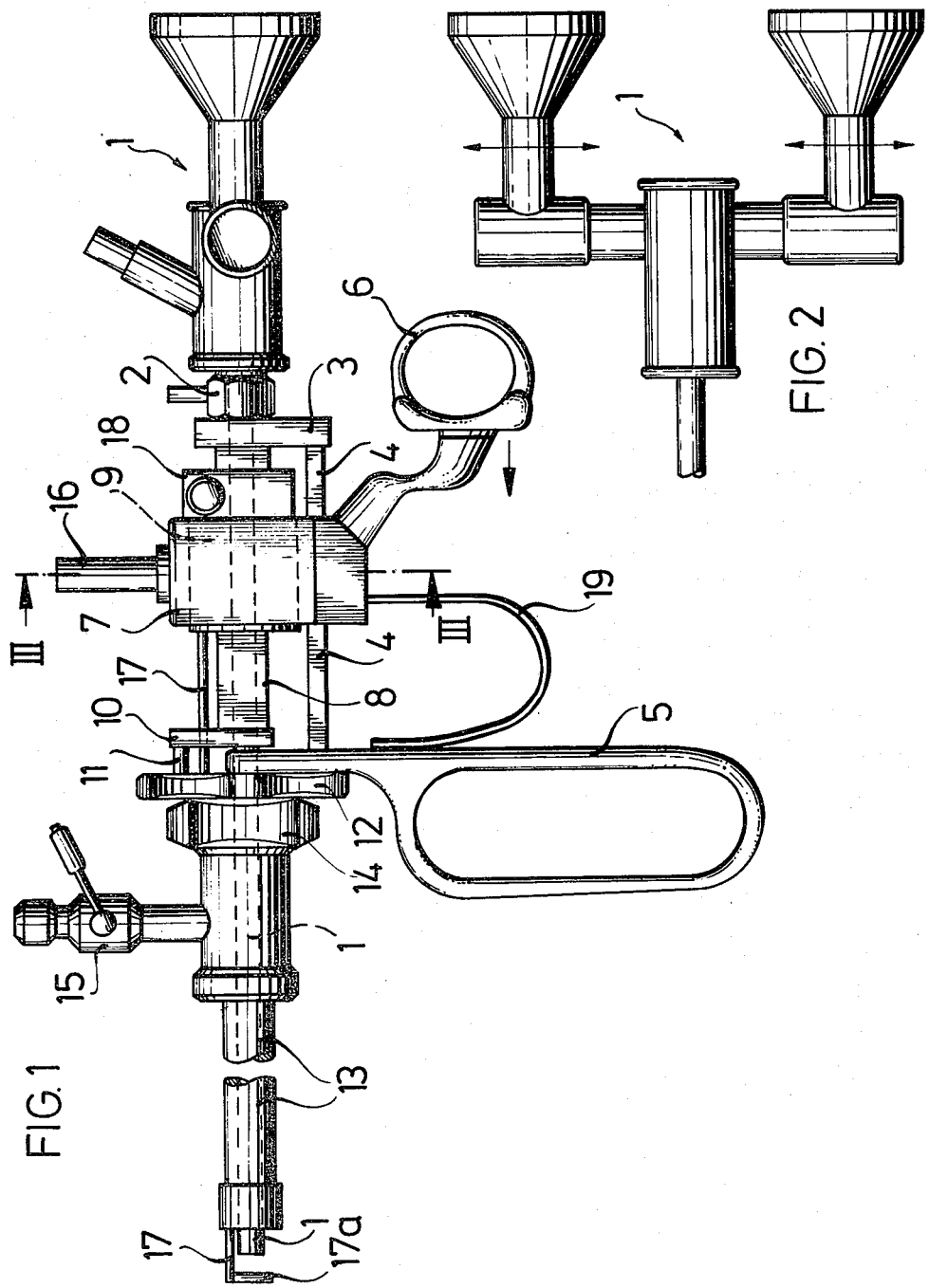

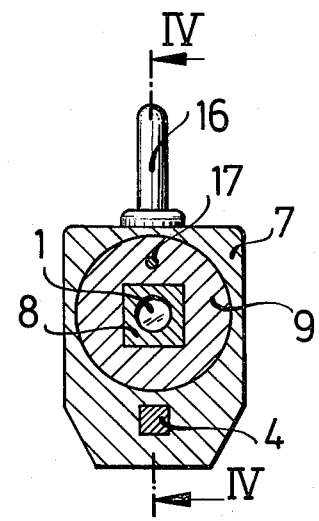
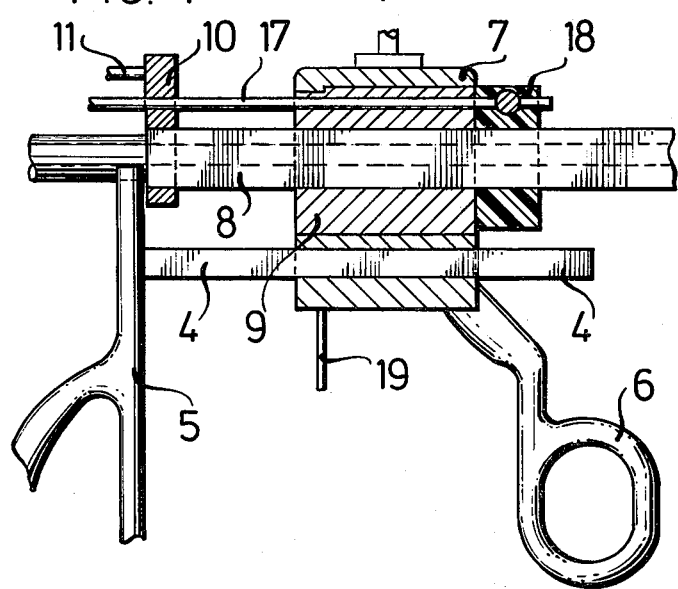

RESECTOSCOPES

BACKGROUND OF THE INVENTION

The present invention relates to a resectoscope of the kind comprising an optical system extending through a shaft and an HF cutting electrode which is axially displaceable by means of a guided bearer on a guide traversing the optical system and is rotatable together with said shaft around the axis of the optical system.

In the case of known resectoscopes of the kind hereinabove referred to, the cutting electrode is turned gradually during resectioning together with the shaft traversed by the optical system and the cutting electrode is always present within the field of view of the optical system, particularly if the direction of view amounts to less than 180°.

Use has already been made successfully in modern endoscopy, of optical stereo systems to obtain stereoscopic images of the object. The invention proposes to use a stereo optical system in a resectoscope of the kind referred to above, and an object of the invention consequently is to provide such a resectoscope in which the two rigidly interconnected eyepies of the stereo optical system are always immobilisable in the horizontal position, i.e. at right angles to the vertical axis of the resectoscope even during rotary displacements of the shaft and of the cutting electrode around the axis of the optical system.

SUMMARY OF THE INVENTION

Accordingly, the invention consists in a resectoscope of the kind described, wherein said optical system is a stereo optical system that provides a viewing angle of 180°, and a cylinder is provided with a fastening device to secure the proximal end of the said cutting electrode said cylinder being rotatably and axially displaceably installed within said guided bearer in said guide traversing said optical system, said guide being of polygonal cross-section and rotatable conjointly with said cutting electrode and said shaft around the axis of said optical system, and in that said guided bearer is complementarily guided on a parallel guide provided with a handle at the distal extremity and connected rigidly at the proximal and via a web to a coupling for connection of said optical stereo system.

With this construction, the distal cutting loop of the cutting electrode always remains within the field of view of the optical system and the two stereo eyepieces of the latter always remain in horizontal or approximately horizontal position, during rotation of the shaft end of the electrode around the optical axis. The angle of rotation of the shaft and of the cutting electrode may amount to say 300°, and this range of rotation may be subdivided at will, the rotary displacement being releasably blocked by a catch, about every 30° for example of the rotational range.

BRIEF DESCRIPTION OF THE DRAWINGS

In order that the invention may be more clearly understood, reference will now be made to the accompanying drawings which show one embodiment being by way of example and in which:

FIG. 1 shows a diagrammatical sideview of a resectoscope in accordance with the invention, FIG. 2 shows an underneath plan view of the proximal section of the optical stereo system utilised, FIG. 3 shows a cross-section along the line III—III of FIG. 1, and FIG. 4 shows a partial axial cross-section corresponding to line IV—IV of FIG. 3.

DETAILED DESCRIPTION OF A PREFERRED EMBODIMENT

Referring now to the drawings, an optical stereo system 1 having an angle of view of 180°, extends through a resectoscope from the proximal end thereof and is rigidly locked by means of a coupling 2 to a web 3 of a guide 4 parallel to the optical axis, said guide being fitted with a handle 5 and supporting a guided bearer 7 provided with an actuating ring 6 to prevent a tipping action. The bearer 7 is primarily guided in axially displaceable manner on a hollow polygonal-section rail or bar 8 loosely traversed by the optical system 1, that is to say by virtue of the fact that a cylinder 9 which is guided axially displaceably on the polygonal rail 8 by means of a co-axial polygonal perforation, is rotatably mounted within the guided bearer 7. The polygonal-section rail 8 is rotatably installed at its front side on the web 3, and at the distal end is also mounted rotatably in the handle 5, the polygonal-section rail being rigidly connected at the distal end to a radial arm 10 which is firmly connected by an axially parallel pin 11 to a manually rotatable annular plate 12. This plate 12 which has to be operated, is provided at the distal end with an axially transpierced coupling cone traversed by the optical system 1, which engages in a matching conical recess of a lockable coupling member 14 carrying the resectoscope shaft 13. The shaft 13 is provided with a flushing or scavenging connector of known kind which may also be rotatable.

The cylinder 9 which is rotatable within the guided bearer 7 which is provided with an HF connector 16, is traversed by the proximal end of a cutting electrode 17 which is connected to a fastening device 18 of the cylinder 9. The cutting electrode 17 traverses the shaft 13 eccentrically between the co-axial optical system and the shaft 13 and is terminated at the distal end by a loop 17a which is known per se.

By grasping the two handle elements 5 and 6, the bearer 7 may be displaced axially against a spring 19, to extend the cutting electrode outwards at the distal end, the displacement of the cutting loop being stereoscopically observable by means of the optical system 1, that is to say also the return cutting movement of the cutting loop, which is caused by the spring 19.

During resectioning, a rotary displacement of the shaft 13 and of the cutting loop 17a around the optical system 1 is needed in most cases, during which the stereo optical system should retain its position with horizontal setting of both eyepieces. This is easily possible by turning the manually operated disc 12, since the shaft 13 with the cutting electrode 17 may be turned via the connection 10, 11 together with the polygonal-section guide 8 and the cylinder 9 around the optical system shaft in the guided bearer 7. In the horizontal position of the eyepieces, the optical system 1 is held in the right-angled position by grasping the handles 5, 6.

I claim:

1. In a resectoscope of the kind comprising an optical system extending through a shaft and an HF cutting electrode which is axially displaceable by means of a guided bearer on a guide traversing the optical system, said electrode being rotatable together with said shaft around the axis of the optical system, the improvement in that said optical system is a stereo system that provides a viewing angle of 180°, and a cylinder is provided with a fastening device securing the proximal end of said cutting electrode, said cylinder being rotatably installed within said guided bearer, said guide being of polygonal cross-section and rotatable conjointly with said cutting electrode and said shaft around the axis of said optical system, and in that said guided bearer is guided on a second guide provided with a handle at the distal extremity and connected rigidly at the proximal end to a coupling of said optical stereo system, whereby the electrode and shaft may be rotated about the axis of the optics while the optics is held in a stationary plane by said handle and second guide.

2. A resectoscope according to claim 1, wherein said polygonal guide is rigidly connected at the distal end, by means of a radial lever arm and an axially parallel pin, to a handwheel which is connectable to said shaft by a coupling, said cutting electrode extending between said shaft and a tube enclosing said optical system.

3. A resectoscope according to claim 1 or 2, wherein a lock for locking the proximal end of said electrode is connected to said cylinder which is rotatable in said bearer.

* * * * *